(12) United States Patent
Chou et al.

(10) Patent No.: US 6,903,200 B1
(45) Date of Patent: Jun. 7, 2005

(54) HUMAN α1 CHAIN COLLAGEN

(75) Inventors: Min-Yuan Chou, Taipei Hsien (TW); Charng-Yih Leu, Taipei Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 154 days.

(21) Appl. No.: 09/996,611

(22) Filed: Nov. 30, 2001

(30) Foreign Application Priority Data

Dec. 27, 2000 (TW) .................................. 89128027 A

(51) Int. Cl.$^7$ .................. C07H 21/02; C12N 15/00; C07K 14/00
(52) U.S. Cl. .............. 536/23.5; 530/350; 530/356; 514/12; 435/320.1; 435/252.33; 435/325
(58) Field of Search .............. 536/23.5; 435/320.1, 435/252.33, 325; 530/350, 356; 514/12

(56) References Cited

U.S. PATENT DOCUMENTS 6,569,662 B1 * 5/2003 Tang et al. ................. 435/212

FOREIGN PATENT DOCUMENTS

WO    WO 01/12659 A2    2/2001

OTHER PUBLICATIONS

Greenspan et al., GenBank Accession No. M76730, Apr. 1993.*
Wiemann, S. et al., Toward a Catalog of Human Genes and proteins: Sequencing and Analysis of 500 Novel Complete Protein Coding Human cDNAs; Genome Research, vol. 11, pp. 422–435.
Duesterhoeft, A., et al., Direct Submission; MIPS, Am Klopferspitz 18a, D–82152, Mar. 12, 2002, Martinsried, Germany.
Min–Yuan Chou et al.; Genomic Organization and Characterization of the Human Type XXI Collagen (COL21A1) Gene; Genomics, 2002, P 395–401, vol. 79, No. 3.

* cited by examiner

*Primary Examiner*—Jon P. Weber
*Assistant Examiner*—Chih-Min Kam
(74) *Attorney, Agent, or Firm*—Fei-Fei Chao; Bingham McCutchen LLP

(57) ABSTRACT

The invention discloses a nucleic acid encoding a human α1 chain collagen, the recombinant vector comprising the same, and the uses therefor. The invention also features a method for producing the protein recombinantly.

9 Claims, 9 Drawing Sheets

FIG. 3

☐ von Willebrand factor A domain

▨ Thrombospondin N-terminal-like domain

■ Collagenous domain

HUMAN α1 CHAIN COLLAGEN

BACKGROUND OF THE INVENTION

1. Field of the Invention

The present invention relates to a novel human collagen protein and a polynucleotide sequence, which encodes the novel human collagen protein. More particularly, it relates to polynucleotides encoding human α1 chain collagen and derivatives thereof.

2. Description of the Related Art

Collagens are structure proteins that participate in the assembly of various kinds of polymers in the extracellular matrix. Collagen polypeptides contain one or more blocks of (Gly-x-y) repeat, in which x represents any amino acid residue, and y frequently represents prolyl or hydroxyprolyl residues. The presence of such sequence repeats allows groups of three collagen polypeptides to fold into triple-helical domains, which are rigid and inextensible.

So far, 20 distinct types of homo-and heterotrimeric molecules, encoded by more than 30 genes, have been identified in vertebrates. These proteins exhibit considerable diversity size, sequences, tissue distribution, molecular composition, and each plays a different structure role in connective tissue.

Within the superfamily of collagens, two categories are classified. The fibrillar collagens include types I, II, III, V, and XI collagen. The triple-helical domains of the proteins polymerize in a staggered fashion to form fibrils. Members of other collagens do not by themselves form cross-striated fibrils, but may be associated with fibrils (FACIT or fibril associated collagens with interrupted triple helices), including types IX, XII, XIV, XVI, and XIX collagen. The structure of these molecules comprises two or more relatively short triple-helical (COL) domains connected and flanked by non-triple-helical (NC) sequences. Type IX collagen is the best-characterized molecule in the members. Studies of transgenic mice with mutations in type IX collagen have been proposed that it acts as molecular bridges between cartilage collagen fibrils and other matrix components, perhaps proteoglycans. The COL domains and the central NC domains of this molecule interact with type II collagen through covalent cross-links to form fibrils. The amino-terminal NC domain has a potential of interacting with other extracellular components. Also, in vitro studies have demonstrated that the N-terminal non-triple-helical domains of type XII and XIV collagen promote contraction of collagen gels. However, the detailed interactions of the bridging hypothesis are not clear.

Collagens are typical mosaic proteins containing a number of shuffled domains. These domains have been classified by sequence similarity in order to characterize their structural and functional relationships to other proteins. This analysis provides an overview of homologies of collagen domains. It also reveals two new relationships: (i) a module common to type V, IX, XI, and XII collagens was found to be homologous to the heparin binding domain of thrombospondin; (ii) the modular architecture of a human type VII collagen fragment was identified. Its N-terminal globular domain contains fibronectin type III repeats located adjacent to a von Willebrand factor type A module. The proposed structural similarities point to analogous subfunctions of the respective domains in otherwise distinct proteins.

Thrombospondin is one of a class of adhesively homotrimeric glycoproteins that mediate cell-to-cell and cell-to-matrix interactions. It is expressed in extracellular matrix, and may have autocrine growth regulatory properties involved in platelet aggregation, embryogenesis, morphogenesis, cell adhesion molecule, major activator of TGFβ1. The von Willebrand factor A (vWF) like domain is the prototype for a protein superfamily and it is found in various proteins including plasma complement factors, integrands, collagens, and other extracellular proteins. Proteins that incorporate vWF domains participate in numerous biological events, such as cell adhesion, migration, homing, pattern formation, and signal transduction.

Collagens are important bio-medical building blocks with the functions of tissue growth, anaplasty, dressing for burn, and wound healing, etc., and the requirements thereof expand largely. Therefore, there is still a need to develop a novel collagen and the derivatives thereof having more therapeutic value and diversity for the various applications.

The present inventors have successfully cloned a novel human α1 chain collagen gene by way of known human expression sequence tag (EST) in combination with bio-informatics and molecular cloning techniques. After comparison of the inventive collagen with the existent 20 collagens, the highest sequence homology is less than 30%, indicating the collagen of the invention is a novel form.

Blood vessels are tubes of endothelial cells surrounded by layers of smooth muscle cells and connective tissue proteins. During development this complex structure forms as a result of biochemical signals between endothelial cells and smooth muscle cells. Sometimes this biochemical communication fails and abnormal blood vessels form. By analyzing gene mutations causing such vascular abnormalities, it can be learned about the signals necessary for normal blood vessel development. In addition, identification of genes responsible for inherited vascular malformations provides a basis for development of rational therapies in the clinical treatment of vascular disorders.

SUMMARY OF THE INVENTION

It is therefore the primary object of the present invention to provide an isolated nucleic acid (hCOLA1) and the degenerate sequences thereof, which encodes human α1 chain collagen protein, comprising the nucleotide sequence set forth in SEQ ID NO: 5. The present invention also provides the expression profile of the isolated collagen gene and the exact tissue and cellular localization of this collagen protein. Moreover, the present invention provides nucleotide fragments derived from SEQ ID NO: 5 as a nucleic acid probe or primer.

In one preferred embodiment, the present invention provides a novel human α1 chain collagen protein encoded by the nucleic acid mentioned above, which has the amino acid sequence set forth in SEQ ID NO: 1.

Another aspect of the present invention provides a recombinant vector comprising the nucleic acid mentioned above and a regulatory sequence.

Still another aspect of the present invention provides a method for producing human α1 chain collagen protein, comprising the steps of: (a) transforming or transfecting a host cell with the recombinant vector described above; (b) culturing said transformed or transfected cell under the conditions sufficient for expression of the human α1 chain collagen protein; and (c) recovering and purifying the human α1 chain collagen protein.

Yet still another aspect of the present invention provides a diagnostic kit for detecting the disease related to the mutation of SEQ ID NO: 5 in a mammal or human, comprising the nucleic acid probe or primer described above.

BRIEF DESCRIPTION OF THE DRAWINGS

The present invention will be more fully understood and further advantages will become apparent when reference is made to the following description of the invention and the accompanying drawings in which:

FIG. 3 is a diagram showing the complete nucleotide sequence (SEQ ID NO: 5) and the corresponding amino acid sequence (SEQ ID NO: 1) of the human α1 chain collagen of the invention.

FIG. 9A shows SDS-PAGE analysis, wherein the numbers indicated are molecular weight standards; lane 1 is the non-induced cell lysate; lane 2 is the cell lysate induced by IPTG for 2 hours; and lane 3 is the cell lysate induced for 3 hours. FIG. 9B, lane 1 shows the human α1 chain collagen protein purified by Ni-column and stained with Coomassie brilliant blue; and lanes 2 and 3 are western blot detected by anti-histidine antibody, wherein lane 2 is the non-induced cell lysate and lane 3 is the cell lysate induced by IPTG for 2 hours without purification.

DETAILED DESCRIPTION OF THE INVENTION

The present invention screened the most conserved regions of the known collagen nucleic acid sequences from human expressed sequence tag (EST) library. A novel biomolecule with the highest homology of the primary amino acid sequence was then found by introducing the sequence of that region into EST library. A full-length cDNA sequence of the novel bio-molecule was then obtained and determined by the technologies of bio-informatics and molecular cloning.

At the beginning, a 57-bp fragment of the conserved region was aligned in the human EST library to obtain a fragment with about 300 bp in length. The fragment was then introduced into Genbank Blast for searching human non-redundant genes to obtain a fragment with about 146 kb in length containing exons and introns. Possible open reading frames were analyzed and the relative oligonucleotide probes were thus designed to clone the novel full-length human α1 chain collagen. The method of cloning will be further described in the following examples.

Figure 3:
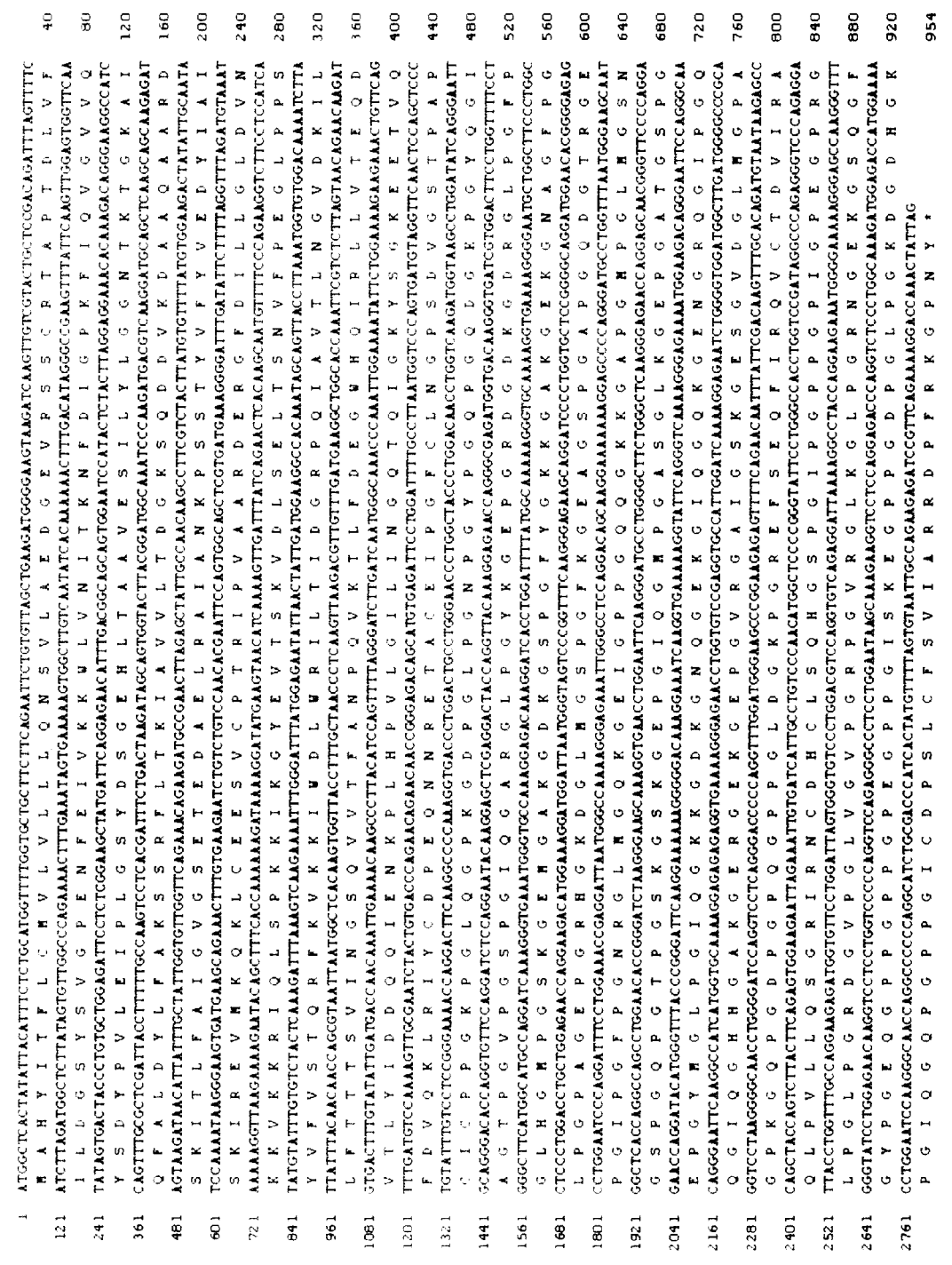

The nucleic acid sequence of the full-length human α1 chain collagen (hCOLA1) gene and the deduced amino acid sequence thereof are shown in FIG. 3 SEQ ID NO: 5 and SEQ ID NO: 1, respectively). The novel human α1 chain collagen gene comprises 2,865 bp, which encodes 954 amino acids with about 99,000 Da in molecular weight, and is located at the p11.2–12.3 on human chromosome VI.

The above isolated nucleic acid (hCOLA1 gene) comprises at least the nucleotide sequence set forth in SEQ ID NO: 5 (including DNA and RNA sequences) or the complementary sequences thereto, and the genomic DNA sequence. Those skilled in this art will be aware that the nucleotide sequences can be modified in accordance with any method known in the art, and are also within the scope of the invention. For example, degenerate codons can be used to replace the relative positions but the gene encodes the same amino acid sequence. Further, additional codons can be inserted into the sequence or added either at the 3'-or 5'-end, but the activity of the protein is not affected or slightly affected. Accordingly, the complementary sequences and degenerate sequences of SEQ ID NO: 5, and various modified variants are included in the present invention. See, for example, Sambrook, et al., Molecular Cloning, A Laboratory Manual, Cold Spring Harbor Laboratory Press, New York, 1989.

Figure 5:
FIG. 5 is a schematic diagram showing domain structure of the human α1 chain collagen protein of the invention.

In accordance with the present invention, the human α1 chain collagen encoded by the isolated hCOLA1 gene comprises three domains (as shown in FIG. 5), including (i) von Willebrand factor A domain (having amino acid sequence set forth in SEQ ID NO: 2); (ii) thrombospondin N-terminal-like domain (having amino acid sequence set forth in SEQ ID NO: 3); and (iii) collagenous domain (having amino acid sequence set forth in SEQ ID NO: 4). To analyze the primary sequence of the protein and to compare with other known 20 collagens, the human α1 chain collagen of the present invention belongs to FACIT family (fibril associated collagens with interrupted triple helices). From the domains described above, it is inferred that the physiological functions of the human α1 chain collagen of the invention may be involved in platelet aggregation, cell adhesion, and the activation of transformation growth factor. In addition, the N-termninal of the collagen protein further includes a signal peptide with 22 amino acids in length. It is inferred that the human α1 chain collagen of the invention is located in the extracellular matrix.

The present invention also provides a recombinant vector comprising the nucleic acid cloned and isolated above, and optionally a regulatory sequence, such as replication region, selection marker (e.g. antibiotic resistance marker), eukaryotic cell promoter or a prokaryotic cell promoter so that the recombinant vector can be expressed in a suitable host, for example, eukaryotic cells such as mammalian cells or yeast, or prokaryotic cells such as *Escherichia coli*.

In one preferred embodiment, the present invention provides a recombinant vector in which the hCOLA1 gene is cloned into Bluescript KS(+) vector (Stratagene). The recombinant vector is deposited at the Culture Collection and Research Center (Food Industry Research and Development Institute, 331 Shih-Pin Road, Hsinchu, Taiwan) on Nov. 14, 2000, and assigned accession number CCRC 940331.

One can produce the novel human α1 chain collagen protein which have the amino acid sequence set forth in SEQ ID NO: 1 using the isolated nucleic acid described above by any suitable method in any suitable expression system known in this art. Therefore, the method for producing the human α1 chain collagen protein is also within the scope of the present invention.

One preferred expression system for the recombinant production of the collagen of the invention is in transgenic non-human animals, wherein the desired collagen may be recovered from the milk of the transgenic animal. Such a system is constructed by linking the DNA sequence encoding the collagen of the invention to a promoter and other required or optional regulatory sequences capable of effecting expression in mammary gland. Likewise, required or optional post-translational enzymes may be produced simultaneously in the target cells, employing suitable expression system operable in the targeted milk protein producing mammary gland cells.

In one preferred embodiment of the present invention, the nucleic acid of SEQ ID NO: 5 is subcloned into an expression vector to obtain another recombinant vector. A suitable host cell (for example, eukaryotic or prokaryotic cell) is then transformed or transfected with the recombinant vector. The transformed or transfected cells are then cultured under the conditions sufficient for expression of human α1 chain collagen protein. Finally, the expressed proteins are recovered and purified. Those skilled in this art will appreciate that the recovering and purifying method is not limited, for example, by various chromatographies. Preferably, the human α1 chain collagen is expressed using histidine tag fusion protein technique, and the recovering and purifying method is performed by affinity column.

As used herein, the term "transformation" or "transfection" includes a variety of techniques for introducing an exogenous nucleic acid into a cell (for example, eukaryotic or prokaryotic), including calcium phosphate or calcium chloride precipitation, microinjection, DEAE-dextrin-mediated transfection, lipofection, or electroporation.

Electroporation is carried out at approximate voltage and capacitance (and corresponding time constant) to result in enter of the DNA construct(s) into the host cells. Electroporation can be carried out over a wide range of voltages (e.g. 50 to 2,000 volts) and corresponding capacitance. Total DNA of approximately 0.1 to 500 μg is generally used.

Methods such as calcium phosphate precipitation and colubrine precipitation, liposome fusion and receptor-mediated gene delivery can also be used to transfect cells.

The genetic engineering methods mentioned above such as DNA modification, cloning, construction, and isolation of the recombinant vector, protein expression, and purification can be accomplished by those skilled in this art, and which can be seen in, for example, Ausubel F. M., et al., Current Protocols in Molecular Biology, New York, 1992; Sambrook, et al., supra; or Davis, L. G., Methods in Molecular Biology, Elsevier, Amsterdam, NL, 1986.

In one aspect of the present invention, the isolated nucleic acid further includes the fragments derived from SEQ ID NO: 5 or the complementary sequences thereto to be as a nucleic acid probe or primer for detection. Those skilled in the art will be aware that the length of the nucleic acid fragment is not limited. For example, as a nucleic acid probe, the fragment preferably comprises at least 500 contiguous nucleotides in length derived from SEQ ID NO: 5 or more, while as a nucleic acid primer, the fragment preferably comprises at least 20 contiguous nucleotides in length derived from SEQ ID NO: 5 or more. The selection of the length of fragment is dependent upon the conditions of detection method as described below. For example, the temperature and ionic strength used in hybridization, or the temperature used in polymerase chain reaction (PCR). Generally, the length of the nucleic acid probe is in proportion to the specificity of the detection result. Accordingly, the nucleic acid probe preferably comprises at least 500 contiguous nucleotides in length derived from SEQ ID NO: 5, and more preferably comprises the full-length nucleic acid of SEQ ID NO: 5. In addition, the length of the nucleic acid primer is in proportion to the specificity of the detection result. Accordingly, the nucleic acid primer preferably comprises at least 20 contiguous nucleotides in length derived from SEQ ID NO: 5, and more preferably comprises 20–25 contiguous nucleotides, thereby increasing the specificity of the detection result.

The human α1 chain collagen polynucleotide of the present invention may be used for diagnostic and/or therapeutic purposes. For diagnostic uses, the polynucleotide of the invention may be used to detect the human α1 chain collagen gene expression or aberrant α1 chain collagen gene expression in disease states, e.g., rheumatoid arthritis, osteoarthritis, reactive arthritis, autoimmune bearing disease, cartilage inflammation due to bacterial or viral infections (e.g. Lyme's disease), parasitic disease, bursitis, corneal diseases, ankylosing spondylitis (fusion of the spine), and cardiovascular disease.

In the present invention the inventor suggested the novel collagen is derived from blood vessels, and maybe relates to cardiovascular disease. By analyzing gene mutations causing cardiovascular abnormalities, it can provide a basis for development of rational therapies in the clinical treatment of cardiovascular disorders.

The kit of the present invention used for detecting such diseases comprises a probe or primer described above. Methods for detecting the expression of hCOLA1 gene by using the nucleic acid probe include, but are not limited to, Northern analysis, Southern analysis, in situ hybridization, and bio-chip/microarray, etc., which are well known in the art. Those skilled in the art will appreciate that methods using the complementary properties between two nucleic acid molecules are within the scope of the present invention. In addition, methods for detecting the expression of hCOLA1 gene by using the nucleic acid primer include, but are not limited to, reverse transcriptase polymerase chain reaction (RT-PCR), 5'-Rapid Amplification of cDNA End (5'-RACE), and 3'-RACE, etc. Those skilled in the art will appreciate that methods using the at least one primer in combination with PCR are also within the scope of the present invention.

The human α1 chain collagen gene and/or protein of the present invention may be useful in the treatment of various abnormal conditions. By introducing gene sequences into cells, gene therapy can be used to treat conditions in which the cells underexpress normal α1 chain collagen or express abnormal/inactive α1 chain collagen. In some instance, the polynucleotide sequence encoding the human α1 chain collagen of the invention is intended to replace or act in the place of a functionally deficient endogenous gene. Alternatively, abnormal conditions characterized by overproliferation can be treated using the antisense of the human α1 chain collagen coding sequence of the invention. Recombinant gene therapy vectors, such as viral vectors, may be engineered to express the human α1 chain collagen of the invention. Thus recombinant gene therapy vectors may be used therapeutically for treatment of diseases resulting from aberrant expression or activity of the human α1 chain collagen of the invention.

Without intending to limit it in any manner, the present invention will be further illustrated by the following examples.

EXAMPLE

Example 1
cDNA Cloning of hCOLA1

A Clontech SMART RACE cDNA Amplification kit was used to clone hCOLA1 cDNA. Sequence specific primers used for the following RACE reactions were either deduced from the previously published partial human genomic clone 682J15 (Genbank Accession No. AL034452) or the cloned hCOLA1 cDNA fragment. Initially, first strand cDNA was synthesized from 1 µg of total RNA pool (Clontech) using Superscript II reverse transcriptase with a specific primer 5'-GGTTCACCTTTGCTTCCCTTAG-3' (SEQ ID NO: 6), deduced from the clone 682J 15. The reaction was following to the manufacture's protocol. The above reverse transcription reaction mixture was used for 5'RACE reaction with a sequence specific primer (5'-TTGGCCCATTAATCCTCGGTTTC-3' (SEQ ID NO: 7)), corresponding to nucleotides 1823–1845 of the hCOLA1 cDNA and the universal primer provided by the kit. All assays were performed in a 50-µl reaction volume using the GeneAmp PCR system 9600 (Perkin-Elmer Cetus).

Figure 1:
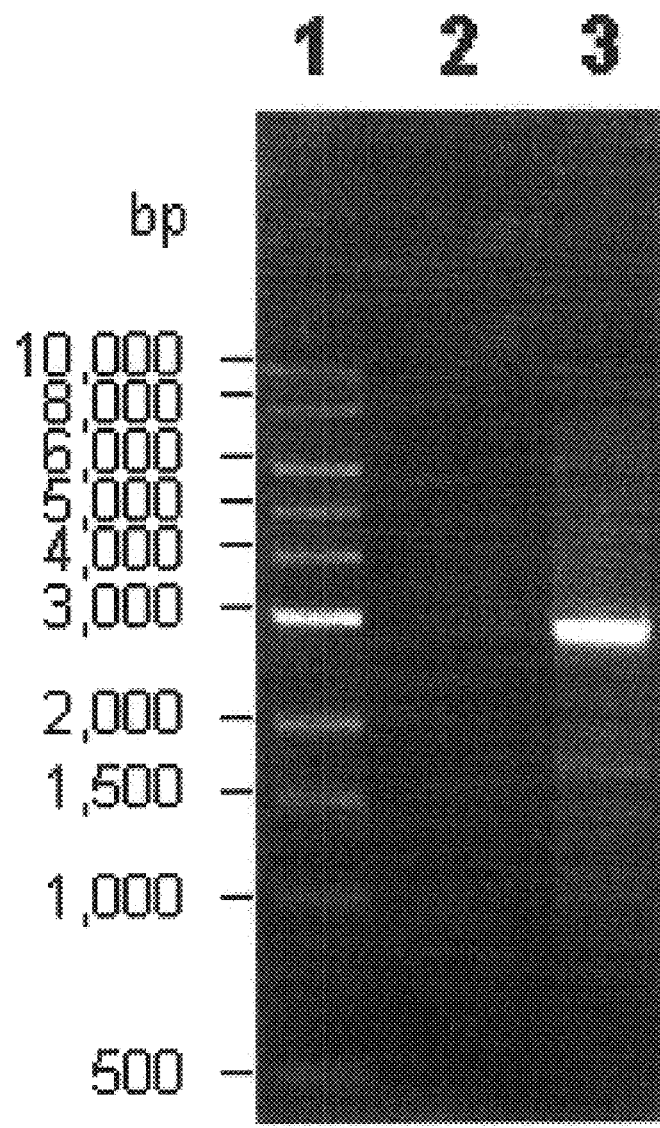
FIG. 1 is a diagram showing the PCR cloning for the human α1 chain collagen cDNA of the invention, wherein lane 1 is the molecular weight markers; lane 2 is the negative control in which the human cDNAs are devoid; and lane 3 is the PCR product containing the cDNA coding for the human α1 chain collagen of the invention.
Figure 2:
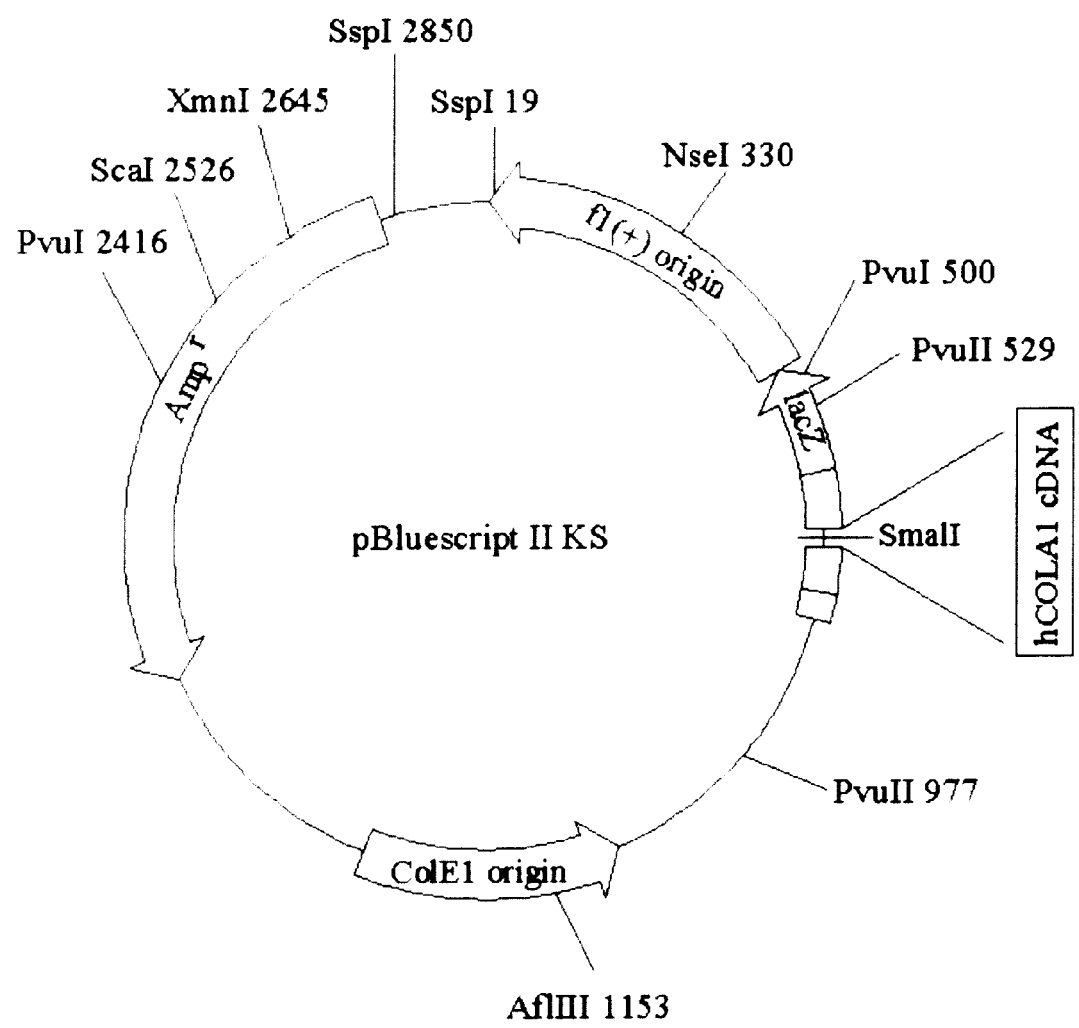
FIG. 2 is a diagram showing the construct of the recombinant vector Bluescript KS(+)/E. coli (hCOLA1) of the present invention.

To obtain the entire coding region of hCOLA1 gene, first strand cDNA was synthesized from 1 µg of total RNA pool (Clontech) using Superscript II reverse transcriptase with an oligo dT primer. After reverse transcription, 1 µl of the reaction mixture was used for PCR amplification with a upstream primer (5'-ATTCCTGGGCCACCTGGTCCGATA-3' (SEQ ID NO: 8)), corresponding to the most 5' candidate initiator methionine of the clone 708F5 (Genbank Accession No. AL031782) and a downstream primer (5'-CTAATAGTTTGGTCCTTTTCT-3' (SEQ ID NO: 9)), corresponding to the 3' stop codon of the clone 682J15. A single band with a molecular size of 2.9 kilo bases was obtained (FIG. 1). The band was excised from gel and cloned into the BlueScript II KS(+) vector (Strategene). The recombinant vector was deposited at the Culture Collection and Research Center (Food Industry Research and Development Institute, 331 Shih-Pin Road, Hsinchu, Taiwan) and assigned accession number CCRC 940331. After nucleotide sequence analysis, the PCR product was found to contain the entire open reading frame of hCOLA1.

Example 2
Nucleotide Sequencing

Nucleotide sequencing was carried out with the Sanger dideoxynucleotide chain termination method (Sambrook, et al., 1989). The sequence samples were prepared using the Ampli Taq cycle sequencing kit (Perkin-Elmer, Inc.) following the manufacturer's protocol. The samples were applied to a 377 automatic sequencer (Perkin-Elmer, Inc.). All reported sequences were confirmed by sequencing of both sense and antisense strands. The full-length nucleotide sequence (SEQ ID NO: 5) and the deduced amino acid sequence (SEQ ID NO: 1) of the human α1 chain collagen of the invention is shown in FIG. 3.

Example 3
Northern Blot Analysis

Figure 6A:
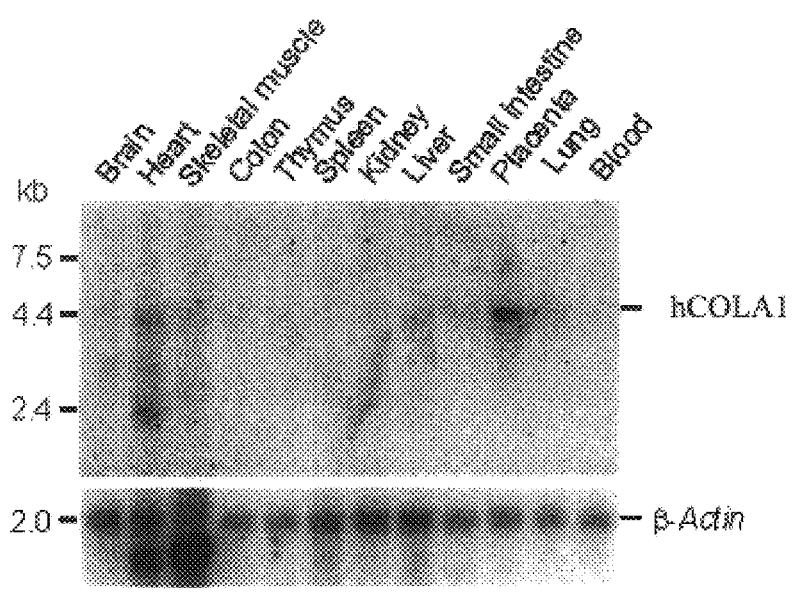
FIG. 6(A) is a Northern blot containing 2 μg of poly(A)$^+$ RNA from indicated tissues hybridized with human α1 chain collagen cDNA-specific probe; and human β-actin-specific probe as an internal control.
Figure 6B:
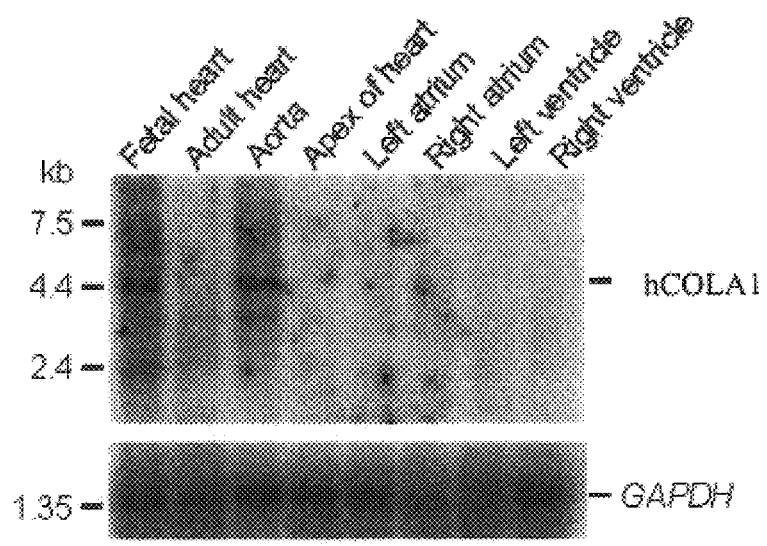
FIG. 6(B) is a Northern blot containing 2 μg of poly(A)$^+$ RNA from indicated cardiovascular tissues hybridized with human α1 chain collagen cDNA-specific probe; and human glyceraldehyde 3-phosphate dehydrogenase (GAPDH) probe as an internal control.

The human multiple tissue and the cardiovascular Northern blots, containing 2 µg of poly(A)$^+$ RNA from indicated tissues, were obtained from Clontech (catalog number 7780-1 and 7791-1, respectively). The blot was hybridized with a randomly primed $^{32}$P-labeled probe corresponding to nucleotides 1236–1863 of the hCOLA1 open reading frame at 60° C. in ExpressHyb solution for one hour and washed with 2×SSC/0.1% SDS two times for 15 min each at 60° C. Then the blot was washed with 0.2×SSC/0.1% SDS three times for 15 min each at 60° C. Human β actin or GAPDH probe was used as a control for the amount of RNA in each lane. As shown in FIG. 6A, a transcript of approximately 4.3 kb is observed, in agreement with the size of the cloned cDNA. The expression of hCOLA1 collagen is mostly confined to placenta and heart tissues, with lower levels in skeletal muscle, small intestine, liver and lung. Another transcript of approximately 2.4 kb was detected to be hybridized with the probe in heart tissue. It probably is a splicing variant of the hCOLA1 gene. We further examined the expression pattern of hCOLA1 in human cardiovascular tissues containing fetal heart and adult heart tissues, together with the aortic and cardiac tissues by Northern blot analysis. Surprisingly, the hCOLA1 transcripts were only present in fetal heart and aortic tissues (FIG. 6B). Moreover, the 2.4 kb short transcript was only present in the fetal heart. Another 7.3 kb band was detected in both tissues. We do not know if this is an additional splicing variant of the hCOLA1 gene. No hybridization signal was detected in adult heart and cardiac tissues. Although the result showing the absence of hCOLA1 transcript in adult heart is inconsistent with the data of Northern blot analysis in FIG. 6A, the hCOLA1 mRNA level in fetal heart is 22-fold in excess of the adult heart based on the quantitative RT-PCR results in FIG. 7 (see below). The presence of the hCOLA1 transcripts in aorta suggests that this novel collagen is derived from blood vessels.

Example 4
Quantitative RT-PCR

Figure 7:
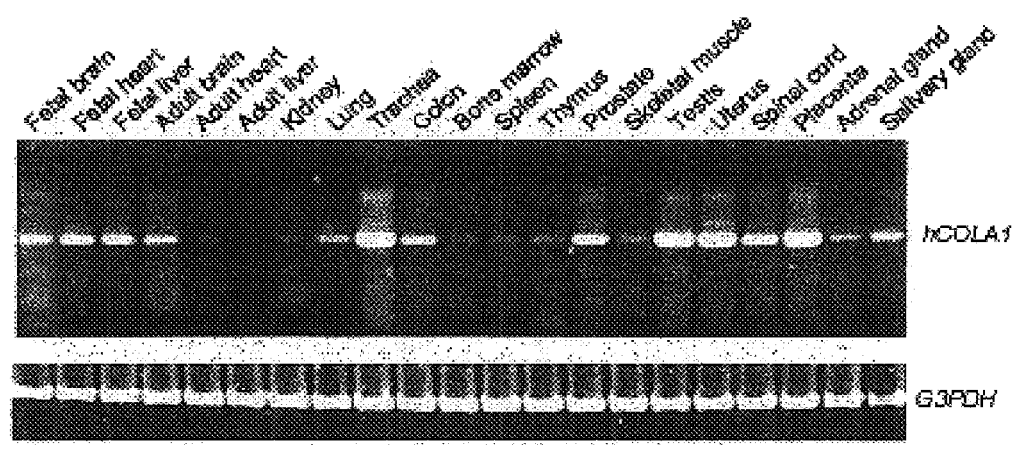
FIG. 7 is a quantitative RT-PCR of the expression of human α1 chain collagen from human fetal and adult tissues. Human glyceraldehyde 3-phosphate dehydrogenase was used as internal control.
Figure 8A:
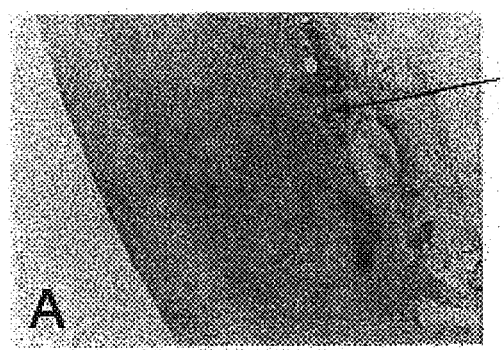
FIGS. 8A, 8B, 8C are in situ in situ hybridization analyses of expression of the human α1 chain collagen mRNA expression. Cardiovascular sections and cells were hybridized with digoxigenin labeled antisense riboprobes for human α1 chain collagen. (A) Longitudinal section, artery; (B) longitudinal section, ventricle; and (C) aortic smooth muscle cells. Control hybridizations labeled with sense probes did not produce signals (data not shown). Bar, 10 μm.
Figure 8B:
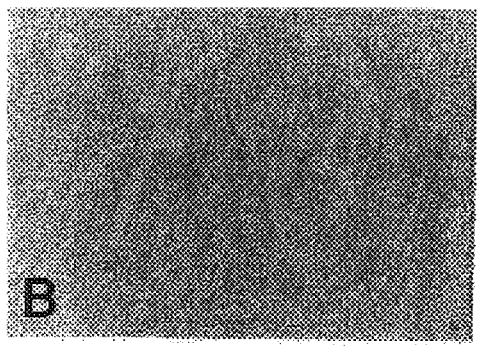
Figure 8C:
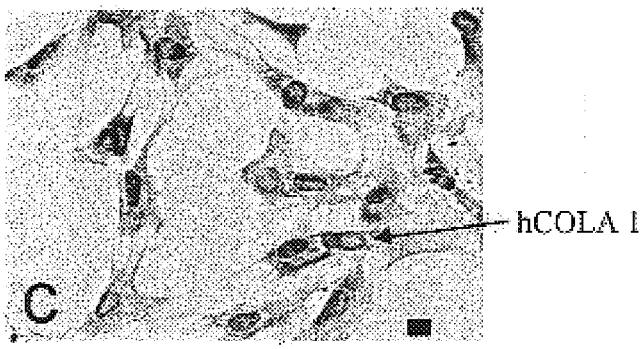

Five micrograms of total RNAs from a variety of human fetal and adult tissues obtained from Clontech (catalog number K4005-1) were used for reverse transcription reactions with oligo (dT) primers. After reverse transcription reactions, the relative quantity of endogenous GAPDH mRNA in each tissue sample was determined with CYBR Green fluorescence dye (Molecular Probes) using Real-time PCR analysis (LightCycler, Roche Molecular Biochemicals). The resulting GAPDH mRNA value in each tissue sample was used to normalize the sample for differences in the amount of total RNA added to each PCR reaction. Each of the normalized tissue samples was then split to perform the target hCOLA1 collagen and control GAPDH amplifications by Real-time PCR analysis. The relative quantity of hCOLA1 collagen cNDA in each reaction was determined in the exponential phase to ensure that the amount of product amplified reflects the quantity of starting mRNA. Primers used for PCR amplifications are as follows: GAPDH (5'-TGAAGGTCGGAGTCAACGGATTTGGT-3' (SEQ ID NO: 10) and 5'-CATGTGGGCCATGAGGTCCACCAC-3' (SEQ ID NO: 11); 983-bp fragment); hCOLA1 collagen (5'-TTCCTGGAAACCGAGGATTAATG-3' (SEQ ID NO: 12) and 5'-AGTCCACGATCACCCTTGTCAC-3' (SEQ ID NO: 13); 1546-bp fragment). Meanwhile, samples at a PCR cycle in the linear range of amplification (30 cycles for hCOLA1; 20 cycles for GAPDH) were electrophoresed on 1.5% agarose and stained with ethidium bromide for visualization. As shown in FIG. 7, when normalized to the GAPDH values, the relative amounts of hCOLA1 transcripts were 2.7, 22 and 30 times more in fetal brain, heart and liver than in the adult counterparts, respectively. The results indicate that hCOLA1 expression is developmentally regulated and suggest a role for hCOLA1 collagen in developmental processes in multiple tissues. Comparison of the hCOLA1 expression in different adult tissues reveals that high levels of hCOLA1 expression were detected in trachea, testis, uterus, and placenta, with modest levels of expression in brain, lung, colon, prostate, spinal cord, and salivary gland. The hCOLA1 collagen mRNA expression was very low or undetectable in adult heart, liver, kidney, bone marrow, spleen, thymus, skeletal muscle, and adrenal gland.

Example 5
In situ Hybridization Analysis

In situ hybridization was performed on 5-µm human cardiovascular tissue sections (Novagen, catalog number 70316-3). An antisense or sense RNA probe labeled with digoxigenin-UTP (DIG-UTP) encompassing the region corresponding to nucleotides 1236–1547 of the hCOLA1 open reading frame was obtained by in vitro transcription (Boehringer RNA labeling kit). Sections were dewaxed by washing three times for 5 min in xylene. After dewaxing, sections were rehydrated to PBS through an ethanol series, washed three times in PBS, and then incubated for 15 min in a proteinase K solution (10 µg/ml in PBS). Proteinase K activity was stopped by washing twice in PBS and sections were refixed at RT for 30 min in 4% paraformaldehyde, 0.2% glutaraldehyde in PBS. After fixation, sections were washed twice in PBS then incubated for 1 h at 50° C. in pre-hybridization mix (50% foramide, 5×SSC, 50 µg/ml yeast tRNA, 0.1% SDS and 50 µg/ml heparin). Hybridization mix containing probe was replaced and incubated at 50° C. for overnight. After hybridization, sections were washed twice for 30 min at 50° C. in solution I (50% foramide, 5×SSC, and 0.1% SDS) and twice for 30 min at 50° C. in solution II (50% foramide, 2×SSC, and 0.1% SDS). Sections were washed three Limes at RT in MAB (100 mM maleic acid, 150 mM NaCl, pH 7.5) and then blocked for 2 h at RT with 2% blocking reagent (Boehringer) in MAB. Sections were incubated for 2 h at RT with 2% blocking reagent in MAB containing 1:2000 dilution of anti-DIG antibody. The sections were washed 4 times for 15 min at RT in MAB-Tween (0.1% Tween-20), washed three times for 5 min in AP buffer (0.1 M Tris-HCl, pH 9.0, 50 mM MgCl$_2$, 0.1 M NaCl, and 0.1% Tween). Color was developed by incubating the sections in NBT/BCIP. After developing, sections were washed in PBS and counterstained with nuclear fast red and then mounted with Histomount Mounting Solution (Zymed). Cells grown on coverslips for in situ hybridization analysis were performed according to the previously published protocol.

Example 6
Expression of hCOLA1 in *Escherichia coli* and Purification

Figure 9A:
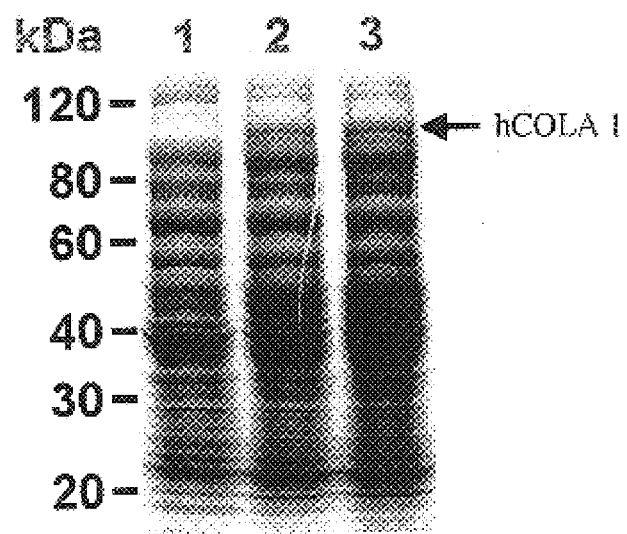
FIGS. 9A and 9B are is a diagram showing the expression of the human α1 chain collagen protein in E. coli.

The entire coding region of the hCOLA1 cDNA was amplified by PCR with primers 5'-ATGGCTCACTATATTACATTTCTC-3' (SEQ ID NO: 14), corresponding to the 5' cDNA region and 5'-TTAGTGATGGTGATGGTGATGCTCATAGTTT GGTCCTTTTCTG-3' (SEQ ID NO:15), corresponding to the 3' region including 6 histidine residues right before the stop codon. The amplified DNA construct was gel purified and sub-cloned into the expression vector pET 15b (Novagen) in which the Nco I site was digested and blunted with Klenow fragment. The recombinant protein was obtained by expressing the constructs in *E. coli* strain BL21 (DE3). The transformed *E. coli* was cultured in LB medium containing 100 µg/ml of ampicillin at 37° C. to reach an optical density of 0.7 at 600 nm, followed by induction with IPTG at a final concentration of 1 mM and kept culturing for an additional 2 or 3 hours. The cell lysate with total proteins was analyzed by SDS-PAGE. The result is shown in FIG. 9A.

Figure 9B:
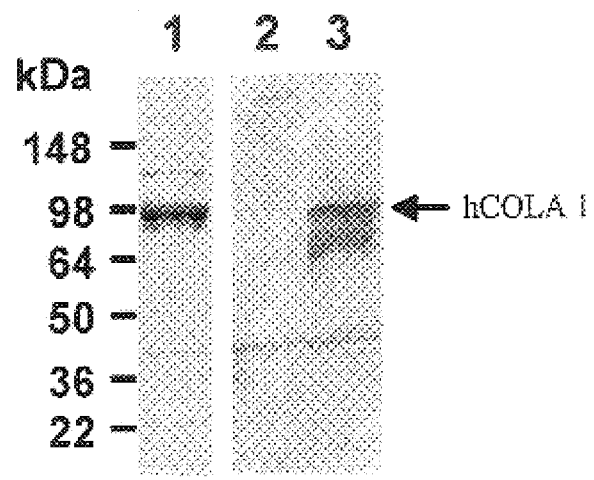

One liter of the IPTG induced *E. coli* cells was cultured for 2 hours and then centrifuged at 5000×g for 30 min. The cell pellet was washed with PBS and centrifuged again. The cell pellet was then re-suspended in 20 ml of PBS containing 1 mM of PMSF. The cell suspension was subjected to ultrasonication to break the cell walls. The cell lysate was then centrifuged at 30,000×g for 40 min. The supernatant was applied to a Ni-agarose column (5 ml in bed volume) that has been equilibrated with 50 mM of Tris-HCl buffer, pH 8.0 at a flow rate 0.5 ml/min. The column was washed with the same buffer containing 40 mM of imidazole. The recombinant hCOLA1 was eluted with the same buffer containing 0.25 M imidazole. The eluate was quantified and analyzed by SDS-PAGE, followed by staining with Coomassie brilliant blue. A protein band with 98 kDa in molecular weight was observed on the gel (FIG. 9(B), lane 1). In addition, the proteins without purification were blotted to a PVDF membrane. An antibody to histidine tag (Clontech) was used to detect the recombinant protein. The result of Western blot is shown in FIG. 9(B), lanes 2 and 3, in which the band indicated at 98 kDa corresponds to the human α1 chain collagen protein of the invention.

Example 7
Expression of hCOLA1 in Eukaryotic Cell

Figure 10:
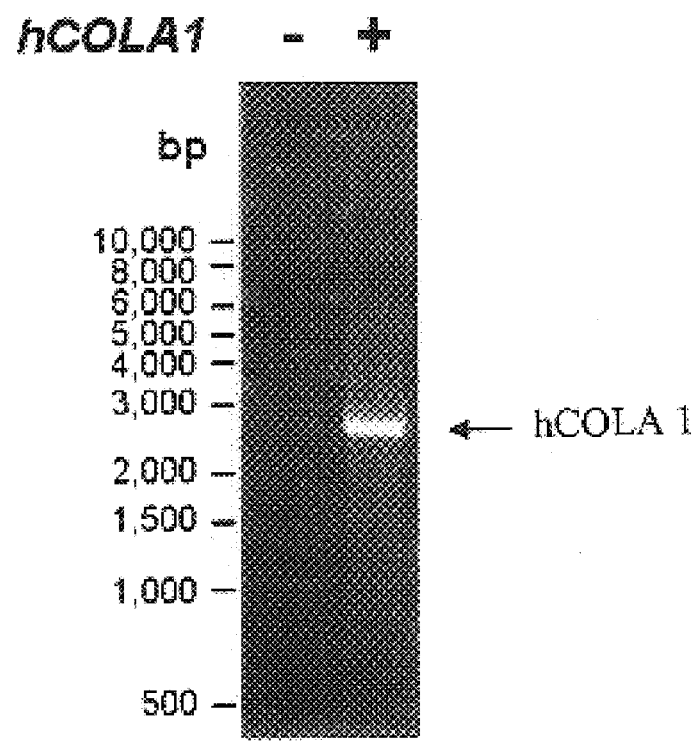
FIG. 10 is a diagram showing RT-PCR of the recombinant expression of human α1 chain collagen in COS7 cells, wherein "−" refers to negative control; "+" is the RT-PCR products from transformants containing human α1 chain collagen gene; and numbers indicated are molecular weight standards.

The hCOLA1 cDNA containing entire open reading frame prepared by Example 4 was gel purified and sub-cloned into the expression vector pcDNA 3.1 containing CMV promoter (Invitrogen) in which the Pme I site was digested and blunted with Klenow fragment. The mammalian cells COS7 were transfected with the expression vector via Superfect (Qiagen), and cultured in DMEM supplemented with 10% FBS (Life Technologies) for 48 hours. About $10^6$ cells were used for the extraction of total RNA. The reverse transcription was performed with oligo dT primer using 0.2 µg RNA as template. After reaction, PCR was carried out with primers T7 and BGHrev on the pcDNA3.1 vector using 0.5 µl solution. The result is shown in FIG. 10, indicating that the vector is expressed in the transfected mammalian cells.

Figure 4:
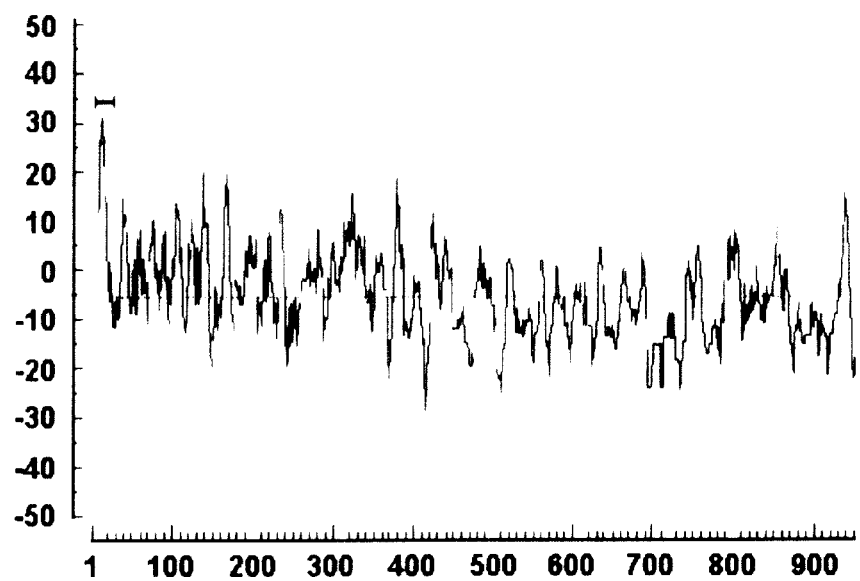
FIG. 4 is a diagram showing the hydropathy profile of the deduced amino acid sequence of SL. Kyte-Doolittle hydrophobicity profile of the human α1 chain collagen plotted with a 11-residue window.

Referring to FIG. 4, the first 22 amino acid residues indicated by a solid bar encode a putative signal peptide characterized by secreted proteins. It is inferred that the human α1 chain collagen protein of the invention is located in the extracellular matrix.

The amino acid sequence of the human α1 chain collagen protein of the invention is compared with those of other 20 known collagens, particularly type IX and type XIX, the most similar in structures. The amino acid sequence identity of collagens between type IX and hCOLA1 of the invention is 24%, while that between type XIX and hCOLA1 of the invention is 27%, indicating that hCOLA I of the invention is a novel form of collegen.

While the invention has been particularly shown and described with the reference to the preferred embodiment thereof, it will be understood by those skilled in the art that various changes in form and details may be made without departing from the spirit and scope of the invention.

What is claimed is:

1. An isolated nucleic acid encoding human α1 chain collagen protein, consisting of the nucleotide sequence set forth in SEQ ID NO:5.

2. A recombinant vector comprising the nucleic acid of claim 1 and an operably linked heterologous regulatory sequence.

3. The recombinant vector as claimed in claim 2, wherein the operably linked regulatory sequence is an operatively linked promoter.

4. The recombinant vector as claimed in claim 2, wherein the recombinant vector is designated Bluescript KS(+)/*E. coli* DH5α(hCOLA1) and deposited at the Culture Collection and Research Center (Hsinchu, Taiwan) and assigned accession number CCRC 940331.

5. A method for producing human α1 chain collagen protein, comprising the steps of:

(a) transforming or transfecting a host cell with the recombinant vector of claim 2;

(b) culturing said transformed or transfected cell under the conditions sufficient for expression of the human α1 chain collagen protein; and (c) recovering and purifying the human α1 chain collagen protein.

6. The method as claimed in claim 5, wherein the host cell is a prokaryotic cell or a eukaryotic cell.

7. The method as claimed in claim 6, wherein the prokaryotic cell is *Escherichia coli*.

8. The method as claimed in claim 6, wherein the eukaryotic cell is a mammalian cell.

9. The method as claimed in claim 6, wherein the recovering and purifying step is conducted by column chromatography.

* * * * *

SEQUENCE LISTING

<160> NUMBER OF SEQ ID NOS: 15

<210> SEQ ID NO 1
<211> LENGTH: 954
<212> TYPE: PRT
<213> ORGANISM: Homo sapiens

<400> SEQUENCE: 1

Met Ala His Tyr Ile Thr Phe Leu Cys Met Val Leu Val Leu Leu Leu
1               5                  10                  15

Gln Asn Ser Val Leu Ala Glu Asp Gly Glu Val Arg Ser Ser Cys Arg
            20                  25                  30

Thr Ala Pro Thr Asp Leu Val Phe Ile Leu Asp Gly Ser Tyr Ser Val
        35                  40                  45

Gly Pro Glu Asn Phe Glu Ile Val Lys Lys Trp Leu Val Asn Ile Thr
    50                  55                  60

Lys Asn Phe Asp Ile Gly Pro Lys Phe Ile Gln Val Gly Val Val Gln
65                  70                  75                  80

Tyr Ser Asp Tyr Pro Val Leu Glu Ile Pro Leu Gly Ser Tyr Asp Ser
                85                  90                  95

Gly Glu His Leu Thr Ala Ala Val Glu Ser Ile Leu Tyr Leu Gly Gly
            100                 105                 110

Asn Thr Lys Thr Gly Lys Ala Ile Gln Phe Ala Leu Asp Tyr Leu Phe
        115                 120                 125

Ala Lys Ser Ser Arg Phe Leu Thr Lys Ile Ala Val Val Leu Thr Asp
    130                 135                 140

Gly Lys Ser Gln Asp Asp Val Lys Asp Ala Ala Gln Ala Ala Arg Asp
145                 150                 155                 160

Ser Lys Ile Thr Leu Phe Ala Ile Gly Val Gly Ser Glu Thr Glu Asp
                165                 170                 175

Ala Glu Leu Arg Ala Ile Ala Asn Lys Pro Ser Ser Thr Tyr Val Phe
            180                 185                 190

Tyr Val Glu Asp Tyr Ile Ala Ile Ser Lys Ile Arg Glu Val Met Lys
        195                 200                 205

Gln Lys Leu Cys Glu Glu Ser Val Cys Pro Thr Arg Ile Pro Val Ala
    210                 215                 220

Ala Arg Asp Glu Arg Gly Phe Asp Ile Leu Leu Gly Leu Asp Val Asn
225                 230                 235                 240

Lys Lys Val Lys Lys Arg Ile Gln Leu Ser Pro Lys Lys Ile Lys Gly
                245                 250                 255

Tyr Glu Val Thr Ser Lys Val Asp Leu Ser Glu Leu Thr Ser Asn Val
            260                 265                 270

Phe Pro Glu Gly Leu Pro Pro Ser Tyr Val Phe Val Ser Thr Gln Arg
        275                 280                 285

Phe Lys Val Lys Lys Ile Trp Asp Leu Trp Arg Ile Leu Thr Ile Asp
    290                 295                 300

Gly Arg Pro Gln Ile Ala Val Thr Leu Asn Gly Val Asp Lys Ile Leu
305                 310                 315                 320

Leu Phe Thr Thr Thr Ser Val Ile Asn Gly Ser Gln Val Val Thr Phe
                325                 330                 335

Ala Asn Pro Gln Val Lys Thr Leu Phe Asp Glu Gly Trp His Gln Ile
            340                 345                 350

Arg Leu Leu Val Thr Glu Gln Asp Val Thr Leu Tyr Ile Asp Asp Gln

-continued

```
                355                 360                 365
Gln Ile Glu Asn Lys Pro Leu His Pro Val Leu Gly Ile Leu Ile Asn
            370                 375                 380
Gly Gln Thr Gln Ile Gly Lys Tyr Ser Gly Lys Glu Thr Val Gln
385                 390                 395                 400
Phe Asp Val Gln Lys Leu Arg Ile Tyr Cys Asp Pro Glu Gln Asn Asn
                405                 410                 415
Arg Glu Thr Ala Cys Glu Ile Pro Gly Phe Cys Leu Asn Gly Pro Ser
                420                 425                 430
Asp Val Gly Ser Thr Pro Ala Pro Cys Ile Cys Pro Pro Gly Lys Pro
                435                 440                 445
Gly Leu Gln Gly Pro Lys Gly Asp Pro Gly Leu Pro Gly Asn Pro Gly
            450                 455                 460
Tyr Pro Gly Gln Pro Gly Gln Asp Gly Lys Pro Gly Tyr Gln Gly Ile
465                 470                 475                 480
Ala Gly Thr Pro Gly Val Pro Gly Ser Pro Gly Ile Gln Gly Ala Arg
                485                 490                 495
Gly Leu Pro Gly Tyr Lys Gly Glu Pro Gly Arg Asp Gly Asp Lys Gly
            500                 505                 510
Asp Arg Gly Leu Pro Gly Phe Pro Gly Leu His Gly Met Pro Gly Ser
            515                 520                 525
Lys Gly Glu Met Gly Ala Lys Gly Asp Lys Gly Ser Pro Gly Phe Tyr
            530                 535                 540
Gly Lys Lys Gly Ala Lys Gly Glu Lys Gly Asn Ala Gly Phe Pro Gly
545                 550                 555                 560
Leu Pro Gly Pro Ala Gly Glu Pro Gly Arg His Gly Lys Asp Gly Leu
                565                 570                 575
Met Gly Ser Pro Gly Phe Lys Gly Glu Ala Gly Ser Pro Gly Ala Pro
            580                 585                 590
Gly Gln Asp Gly Thr Arg Gly Glu Pro Gly Ile Pro Gly Phe Pro Gly
            595                 600                 605
Asn Arg Gly Leu Met Gly Gln Lys Gly Glu Ile Gly Pro Pro Gly Gln
            610                 615                 620
Gln Gly Lys Lys Gly Ala Pro Gly Met Pro Gly Leu Met Gly Ser Asn
625                 630                 635                 640
Gly Ser Pro Gly Gln Pro Gly Thr Pro Gly Ser Lys Gly Ser Lys Gly
                645                 650                 655
Glu Pro Gly Ile Gln Gly Met Pro Gly Ala Ser Gly Leu Lys Gly Glu
                660                 665                 670
Pro Gly Ala Thr Gly Ser Pro Gly Glu Pro Gly Tyr Met Gly Leu Pro
                675                 680                 685
Gly Ile Gln Gly Lys Lys Gly Asp Lys Gly Asn Gln Gly Glu Lys Gly
            690                 695                 700
Ile Gln Gly Gln Lys Gly Glu Asn Gly Arg Gln Gly Ile Pro Gly Gln
705                 710                 715                 720
Gln Gly Ile Gln Gly His His Gly Ala Lys Gly Glu Arg Gly Glu Lys
                725                 730                 735
Gly Glu Pro Gly Val Arg Gly Ala Ile Gly Ser Lys Gly Glu Ser Gly
                740                 745                 750
Val Asp Gly Leu Met Gly Pro Ala Gly Pro Lys Gly Gln Pro Gly Asp
            755                 760                 765
Pro Gly Pro Gln Gly Pro Pro Gly Leu Asp Gly Lys Pro Gly Arg Glu
            770                 775                 780
```

```
Phe Ser Glu Gln Phe Ile Arg Gln Val Cys Thr Asp Val Ile Arg Ala
785                 790                 795                 800

Gln Leu Pro Val Leu Leu Gln Ser Gly Arg Ile Arg Asn Cys Asp His
            805                 810                 815

Cys Leu Ser Gln His Gly Ser Pro Gly Ile Pro Gly Pro Pro Gly Pro
            820                 825                 830

Ile Gly Pro Glu Gly Pro Arg Gly Leu Pro Gly Leu Pro Gly Arg Asp
            835                 840                 845

Gly Val Pro Gly Leu Val Gly Val Pro Gly Arg Pro Gly Val Arg Gly
            850                 855                 860

Leu Lys Gly Leu Pro Gly Arg Asn Gly Glu Lys Gly Ser Gln Gly Phe
865                 870                 875                 880

Gly Tyr Pro Gly Glu Gln Gly Pro Pro Gly Pro Pro Gly Pro Glu Gly
            885                 890                 895

Pro Pro Gly Ile Ser Lys Glu Gly Pro Pro Gly Asp Pro Gly Leu Pro
            900                 905                 910

Gly Lys Asp Gly Asp His Gly Lys Pro Gly Ile Gln Gly Gln Pro Gly
            915                 920                 925

Pro Pro Gly Ile Cys Asp Pro Ser Leu Cys Phe Ser Val Ile Ala Arg
            930                 935                 940

Arg Asp Pro Phe Arg Lys Gly Pro Asn Tyr
945                 950
```

<210> SEQ ID NO 2
<211> LENGTH: 171
<212> TYPE: PRT
<213> ORGANISM: Homo sapiens

<400> SEQUENCE: 2

```
Asp Leu Val Phe Ile Leu Asp Gly Ser Tyr Ser Val Gly Pro Glu Asn
1               5                   10                  15

Phe Glu Ile Val Lys Lys Trp Leu Val Asn Ile Thr Lys Asn Phe Asp
            20                  25                  30

Ile Gly Pro Lys Phe Ile Gln Val Gly Val Val Gln Tyr Ser Asp Tyr
            35                  40                  45

Pro Val Leu Glu Ile Pro Leu Gly Ser Tyr Asp Ser Gly Glu His Leu
            50                  55                  60

Thr Ala Ala Val Glu Ser Ile Leu Tyr Leu Gly Gly Asn Thr Lys Thr
65                  70                  75                  80

Gly Lys Ala Ile Gln Phe Ala Leu Asp Tyr Leu Phe Ala Lys Ser Ser
            85                  90                  95

Arg Phe Leu Thr Lys Ile Ala Val Val Leu Thr Asp Gly Lys Ser Gln
            100                 105                 110

Asp Asp Val Lys Asp Ala Ala Gln Ala Ala Arg Asp Ser Lys Ile Thr
            115                 120                 125

Leu Phe Ala Ile Gly Val Gly Ser Glu Thr Glu Asp Ala Glu Leu Arg
            130                 135                 140

Ala Ile Ala Asn Lys Pro Ser Ser Thr Tyr Val Phe Tyr Val Glu Asp
145                 150                 155                 160

Tyr Ile Ala Ile Ser Lys Ile Arg Glu Val Met
            165                 170
```

<210> SEQ ID NO 3
<211> LENGTH: 183
<212> TYPE: PRT

<213> ORGANISM: Homo sapiens

<400> SEQUENCE: 3

```
Gly Phe Asp Ile Leu Leu Gly Leu Asp Val Asn Lys Val Lys Lys
1               5                   10                  15

Arg Ile Gln Leu Ser Pro Lys Ile Lys Gly Tyr Glu Val Thr Ser
                20                  25                  30

Lys Val Asp Leu Ser Glu Leu Thr Ser Asn Val Phe Pro Glu Gly Leu
                35                  40                  45

Pro Pro Ser Tyr Val Phe Val Ser Thr Gln Arg Phe Lys Val Lys Lys
            50                  55                  60

Ile Trp Asp Leu Trp Arg Ile Leu Thr Ile Asp Gly Arg Pro Gln Ile
65                  70                  75                  80

Ala Val Thr Leu Asn Gly Val Asp Lys Ile Leu Leu Phe Thr Thr Thr
                    85                  90                  95

Ser Val Ile Asn Gly Ser Gln Val Val Thr Phe Ala Asn Pro Gln Val
                    100                 105                 110

Lys Thr Leu Phe Asp Glu Gly Trp His Gln Ile Arg Leu Leu Val Thr
                115                 120                 125

Glu Gln Asp Val Thr Leu Tyr Ile Asp Asp Gln Gln Ile Glu Asn Lys
            130                 135                 140

Pro Leu His Pro Val Leu Gly Ile Leu Ile Asn Gly Gln Thr Gln Ile
145                 150                 155                 160

Gly Lys Tyr Ser Gly Lys Glu Glu Thr Val Gln Phe Asp Val Gln Lys
                    165                 170                 175

Leu Arg Ile Tyr Cys Asp Pro
                180
```

<210> SEQ ID NO 4
<211> LENGTH: 509
<212> TYPE: PRT
<213> ORGANISM: Homo sapiens

<400> SEQUENCE: 4

```
Gly Lys Pro Gly Leu Gln Gly Pro Lys Gly Asp Pro Gly Leu Pro Gly
1               5                   10                  15

Asn Pro Gly Tyr Pro Gly Gln Pro Gly Gln Asp Gly Lys Pro Gly Tyr
                20                  25                  30

Gln Gly Ile Ala Gly Thr Pro Gly Val Pro Gly Ser Pro Gly Ile Gln
            35                  40                  45

Gly Ala Arg Gly Leu Pro Gly Tyr Lys Gly Glu Pro Gly Arg Asp Gly
        50                  55                  60

Asp Lys Gly Asp Arg Gly Leu Pro Gly Phe Pro Gly Leu His Gly Met
65                  70                  75                  80

Pro Gly Ser Lys Gly Glu Met Gly Ala Lys Gly Asp Lys Gly Ser Pro
                    85                  90                  95

Gly Phe Tyr Gly Lys Lys Gly Ala Lys Gly Glu Lys Gly Asn Ala Gly
                100                 105                 110

Phe Pro Gly Leu Pro Gly Pro Ala Gly Glu Pro Gly Arg His Gly Lys
            115                 120                 125

Asp Gly Leu Met Gly Ser Pro Gly Phe Lys Gly Glu Ala Gly Ser Pro
        130                 135                 140

Gly Ala Pro Gly Gln Asp Gly Thr Arg Gly Glu Pro Gly Ile Pro Gly
145                 150                 155                 160

Phe Pro Gly Asn Arg Gly Leu Met Gly Gln Lys Gly Glu Ile Gly Pro
```

```
                        165                 170                 175
Pro Gly Gln Gln Gly Lys Lys Gly Ala Pro Gly Met Pro Gly Leu Met
                180                 185                 190
Gly Ser Asn Gly Ser Pro Gly Gln Pro Gly Thr Pro Gly Ser Lys Gly
                195                 200                 205
Ser Lys Gly Glu Pro Gly Ile Gln Gly Met Pro Gly Ala Ser Gly Leu
            210                 215                 220
Lys Gly Glu Pro Gly Ala Thr Gly Ser Pro Gly Glu Pro Gly Tyr Met
225                 230                 235                 240
Gly Leu Pro Gly Ile Gln Gly Lys Lys Gly Asp Lys Gly Asn Gln Gly
                245                 250                 255
Glu Lys Gly Ile Gln Gly Gln Lys Gly Glu Asn Gly Arg Gln Gly Ile
                260                 265                 270
Pro Gly Gln Gln Gly Ile Gln Gly His His Gly Ala Lys Gly Glu Arg
            275                 280                 285
Gly Glu Lys Gly Glu Pro Gly Val Arg Gly Ala Ile Gly Ser Lys Gly
            290                 295                 300
Glu Ser Gly Val Asp Gly Leu Met Gly Pro Ala Gly Pro Lys Gly Gln
305                 310                 315                 320
Pro Gly Asp Pro Gly Pro Gln Gly Pro Pro Gly Leu Asp Gly Lys Pro
                325                 330                 335
Gly Arg Glu Phe Ser Glu Gln Phe Ile Arg Gln Val Cys Thr Asp Val
                340                 345                 350
Ile Arg Ala Gln Leu Pro Val Leu Leu Gln Ser Gly Arg Ile Arg Asn
            355                 360                 365
Cys Asp His Cys Leu Ser Gln His Gly Ser Pro Gly Ile Pro Gly Pro
        370                 375                 380
Pro Gly Pro Ile Gly Pro Glu Gly Pro Arg Gly Leu Pro Gly Leu Pro
385                 390                 395                 400
Gly Arg Asp Gly Val Pro Gly Leu Val Gly Val Pro Gly Arg Pro Gly
                405                 410                 415
Val Arg Gly Leu Lys Gly Leu Pro Gly Arg Asn Gly Glu Lys Gly Ser
                420                 425                 430
Gln Gly Phe Gly Tyr Pro Gly Glu Gln Gly Pro Pro Gly Pro Pro Gly
            435                 440                 445
Pro Glu Gly Pro Pro Gly Ile Ser Lys Glu Gly Pro Pro Gly Asp Pro
        450                 455                 460
Gly Leu Pro Gly Lys Asp Gly His Gly Lys Pro Gly Ile Gln Gly
465                 470                 475                 480
Gln Pro Gly Pro Pro Gly Ile Cys Asp Pro Ser Leu Cys Phe Ser Val
            485                 490                 495
Ile Ala Arg Arg Asp Pro Phe Arg Lys Gly Pro Asn Tyr
            500                 505

<210> SEQ ID NO 5
<211> LENGTH: 2865
<212> TYPE: DNA
<213> ORGANISM: Homo sapiens

<400> SEQUENCE: 5
atggctcact atattacatt tctctgcatg gttttggtgc tgcttcttca gaattctgtg      60
ttagctgaag atgggaagt aagatcaagt tgtcgtactg ctccgacaga tttagttttc     120
atcttagatg gctcttatag tgttggccca gaaaactttg aaatagtgaa aaagtggctt     180
```

-continued

| | |
|---|---|
| gtcaatatca caaaaaactt tgacataggg ccgaagttta ttcaagttgg agtggttcaa | 240 |
| tatagtgact accctgtgct ggagattcct ctcggaagct atgattcagg agaacatttg | 300 |
| acggcagcag tggaatccat actctactta ggaggaaaca caaagacagg gaaggccatc | 360 |
| cagtttgcgc tcgattacct ttttgccaag tcctcacgat ttctgactaa gatagcagtg | 420 |
| gtacttacgg atggcaaatc ccaagatgac gtcaaggatg cagctcaagc agcaagagat | 480 |
| agtaagataa cattatttgc tattggtgtt ggttcagaaa cagaagatgc cgaacttaga | 540 |
| gctattgcca acaagccttc gtctacttat gtgttttatg tggaagacta tattgcaata | 600 |
| tccaaaataa gggaagtgat gaagcagaaa ctttgtgaag aatctgtctg tccaacacga | 660 |
| attccagtgg cagctcgtga tgaaggggga tttgatattc ttttaggttt agatgtaaat | 720 |
| aaaaaggtta agaaaagaat acagctttca ccaaaaaaga taaaaggata tgaagtaaca | 780 |
| tcaaaagttg atttatcaga actcacaagc aatgttttcc cagaaggtct tcctccatca | 840 |
| tatgtatttg tgtctactca aagatttaaa gtcaagaaaa tttgggattt atggagaata | 900 |
| ttaactattg atggaaggcc acaaatagca gttaccttaa atggtgtgga caaaatctta | 960 |
| ttatttacaa caaccagcgt aattaatggc tcacaagtgg ttacctttgc taaccctcaa | 1020 |
| gttaagacgt tgtttgatga aggctggcac caaattcgtc tcttagtaac agaacaagat | 1080 |
| gtgactttgt atattgatga ccaacaaatt gaaaacaagc ccttacatcc agttttaggg | 1140 |
| atcttgatca atgggcaaac ccaaattgga aaatattctg gaaagaagaa aactgttcag | 1200 |
| tttgatgtcc aaaagttgcg aatctactgt gacccagaac agaacaaccg ggagacagca | 1260 |
| tgtgagattc ctggattttg ccttaatggt cccagtgatg taggttcaac tccagctccc | 1320 |
| tgtatttgtc ctccgggaaa accaggactt caaggcccca aaggtgaccc tggactgcct | 1380 |
| gggaaccctg gctaccctgg acaacctggt caagatggta agcctggata tcagggaatt | 1440 |
| gcagggacac caggtgttcc aggatctcca ggaatacaag gagctcgagg actaccaggt | 1500 |
| tacaaaggag aaccagggcg agatggtgac aagggtgatc gtggacttcc tggttttcct | 1560 |
| gggcttcatg gcatgccagg atcaaagggt gaaatggtg ccaaggaga caaaggatca | 1620 |
| cctggatttt atggcaaaaa gggtgcaaaa ggtgaaaagg ggaatgctgg cttccctggc | 1680 |
| ctccctggac ctgctggaga accaggaaga catggaaagg atggattaat gggtagtccc | 1740 |
| ggtttcaagg gagaagcagg atcccctggt gctccggggc aggatggaac acggggagag | 1800 |
| cctggaatcc caggatttcc tggaaaccga ggattaatgg gccaaagggg agaaattggg | 1860 |
| cctccaggac agcaaggaaa aaaaggagcc ccagggatgc ctggtttaat gggaagcaat | 1920 |
| ggctcaccag gccagcctgg aacaccggga tctaagggaa gcaaaggtga acctggaatt | 1980 |
| caagggatgc ctgggcttc tgggctcaag ggagaaccag gagcaacggg ttccccagga | 2040 |
| gaaccaggat acatgggttt acccgggatt caaggaaaaa aggggacaa aggaaatcaa | 2100 |
| ggtgaaaaag gtattcaggg tcaaagggga gaaatggaa gacagggaat tccagggcaa | 2160 |
| cagggaattc aaggccatca tggtgcaaaa ggagagagag gtgaaaaggg agaacctggt | 2220 |
| gtccgaggtg ccattggatc aaaaggagaa tctggggtgg atggcttgat ggggcccgca | 2280 |
| ggtcctaagg ggcaacctgg ggatccaggt cctcaggac ccccaggttt ggatgggaag | 2340 |
| cccgaagag agttttcaga acaatttatt cgacaagttt gcacagatgt aataagagcc | 2400 |
| cagctaccag tcttacttca gagtggaaga attagaaatt gtgatcattg cctgtcccaa | 2460 |
| catggctccc cggtattcc tgggccacct ggtccgatag gccagagggg tcccagagga | 2520 |
| ttacctggtt tgccaggaag agatggtgtt cctggattag tgggtgtccc tggacgtcca | 2580 |

-continued

```
ggtgtcagag gattaaaagg cctaccagga agaaatgggg aaaaagggag ccaagggttt     2640
gggtatcctg gagaacaagg tcctcctggt cccccaggtc cagagggccc tcctggaata     2700
agcaaagaag gtcctccagg agacccaggt ctccctggca agatggaga ccatggaaaa      2760 cctggaatcc aagggcaacc aggcccccca ggcatctgcg acccatcact atgttttagt     2820
gtaattgcca gaagagatcc gttcagaaaa ggaccaaact attag                      2865
```

<210> SEQ ID NO 6
<211> LENGTH: 22
<212> TYPE: DNA
<213> ORGANISM: artificial sequence
<220> FEATURE:
<223> OTHER INFORMATION: primer deduced from the clone 682J15

<400> SEQUENCE: 6

```
ggttcacctt tgcttccctt ag                                               22
```

<210> SEQ ID NO 7
<211> LENGTH: 23
<212> TYPE: DNA
<213> ORGANISM: artificial sequence
<220> FEATURE:
<223> OTHER INFORMATION: primer, corresponding to nucleotides 1823-1845
      in the hCOLA1 cDNA

<400> SEQUENCE: 7

```
ttggcccatt aatcctcggt ttc                                              23
```

<210> SEQ ID NO 8
<211> LENGTH: 24
<212> TYPE: DNA
<213> ORGANISM: artificial sequence
<220> FEATURE:
<223> OTHER INFORMATION: upstream primer

<400> SEQUENCE: 8

```
attcctgggc cacctggtcc gata                                             24
```

<210> SEQ ID NO 9
<211> LENGTH: 21
<212> TYPE: DNA
<213> ORGANISM: artificial sequence
<220> FEATURE:
<223> OTHER INFORMATION: downstream primer

<400> SEQUENCE: 9

```
ctaatagttt ggtccttttc t                                                21
```

<210> SEQ ID NO 10
<211> LENGTH: 26
<212> TYPE: DNA
<213> ORGANISM: artificial sequence
<220> FEATURE:
<223> OTHER INFORMATION: primer, GAPDH

<400> SEQUENCE: 10

```
tgaaggtcgg agtcaacgga tttggt                                           26
```

<210> SEQ ID NO 11
<211> LENGTH: 24
<212> TYPE: DNA
<213> ORGANISM: artificial sequence
<220> FEATURE:
<223> OTHER INFORMATION: primer, GAPDH

```
<400> SEQUENCE: 11
catgtgggcc atgaggtcca ccac                                          24

<210> SEQ ID NO 12
<211> LENGTH: 23
<212> TYPE: DNA
<213> ORGANISM: artificial sequence
<220> FEATURE:
<223> OTHER INFORMATION: primer, hCOLA1 collagen

<400> SEQUENCE: 12
ttcctggaaa ccgaggatta atg                                           23

<210> SEQ ID NO 13
<211> LENGTH: 22
<212> TYPE: DNA
<213> ORGANISM: artificial sequence
<220> FEATURE:
<223> OTHER INFORMATION: primer, hCOLA1 collagen

<400> SEQUENCE: 13
agtccacgat caccettgtc ac                                            22

<210> SEQ ID NO 14
<211> LENGTH: 24
<212> TYPE: DNA
<213> ORGANISM: artificial sequence
<220> FEATURE:
<223> OTHER INFORMATION: primer for the coding region

<400> SEQUENCE: 14
atggctcact atattacatt tctc                                          24

<210> SEQ ID NO 15
<211> LENGTH: 43
<212> TYPE: DNA
<213> ORGANISM: artificial sequence
<220> FEATURE:
<223> OTHER INFORMATION: primer for the coding region

<400> SEQUENCE: 15
ttagtgatgg tgatggtgat gctcatagtt tggtcctttt ctg                     43
```